United States Patent [19]

Coates

[11] Patent Number: 4,537,591
[45] Date of Patent: Aug. 27, 1985

[54] ADJUSTABLE DIAPER WITH A BACKBAND AND FASTENING PROTECTION MEANS

[76] Inventor: Fredrica V. Coates, 1608 Dublin Rd., Charlottesville, Va. 22903

[21] Appl. No.: 375,231

[22] Filed: May 5, 1982

Related U.S. Application Data

[63] Continuation-in-part of Ser. No. 315,049, Oct. 26, 1981.

[51] Int. Cl.³ .............................................. A61F 13/16
[52] U.S. Cl. ................................ 604/391; 604/385 R
[58] Field of Search .................... 604/390, 391, 385; 428/100; 128/DIG. 15; 2/DIG. 6

[56] References Cited

U.S. PATENT DOCUMENTS

| | | | |
|---|---|---|---|
| 3,063,749 | 11/1962 | Struble et al. | 297/220 |
| 4,051,554 | 10/1977 | Kallman . | |
| 4,055,873 | 11/1977 | Kallman . | |
| 4,058,853 | 11/1977 | Boxer et al. | 428/100 |

Primary Examiner—Stephen C. Pellegrino
Assistant Examiner—Sherri Vinyard
Attorney, Agent, or Firm—Lowe King Price & Becker

[57] ABSTRACT

A diaper (10) according to the invention comprises a conventional, rectangular washable diaper form (12) with opposite inner and outer surfaces (10a, 10b). A pair of attachment tabs (15) each secured to an upper corner of the fabric (12) engage fastening strips (20) secured to the outer surface of the fabric adjacent a lower edge thereof. The fastening strips (20) are elongated and are vertically oriented for adjustable, mating engagement with the attachment tabs (15) to accommodate growth of the infant. The lower edge portion (24) carrying the fastening strips (20) can be folded onto the inner surface (10a) to expose a second elongated fastening strip (25) attachable to tabs (15) to provide a smaller diaper for newborn infants. The backband (30) reinforces the area of attachment of tabs (15) to the diaper form (12). Protective strip portions (50) are provided in several embodiments to cover the hook-bearing attachment surfaces (15a, 19) of the tabs to prevent lint accumulation during washing. A templet (60) is disclosed enabling the conventional diaper (12) to be modified to the diaper (10) of the invention.

23 Claims, 15 Drawing Figures

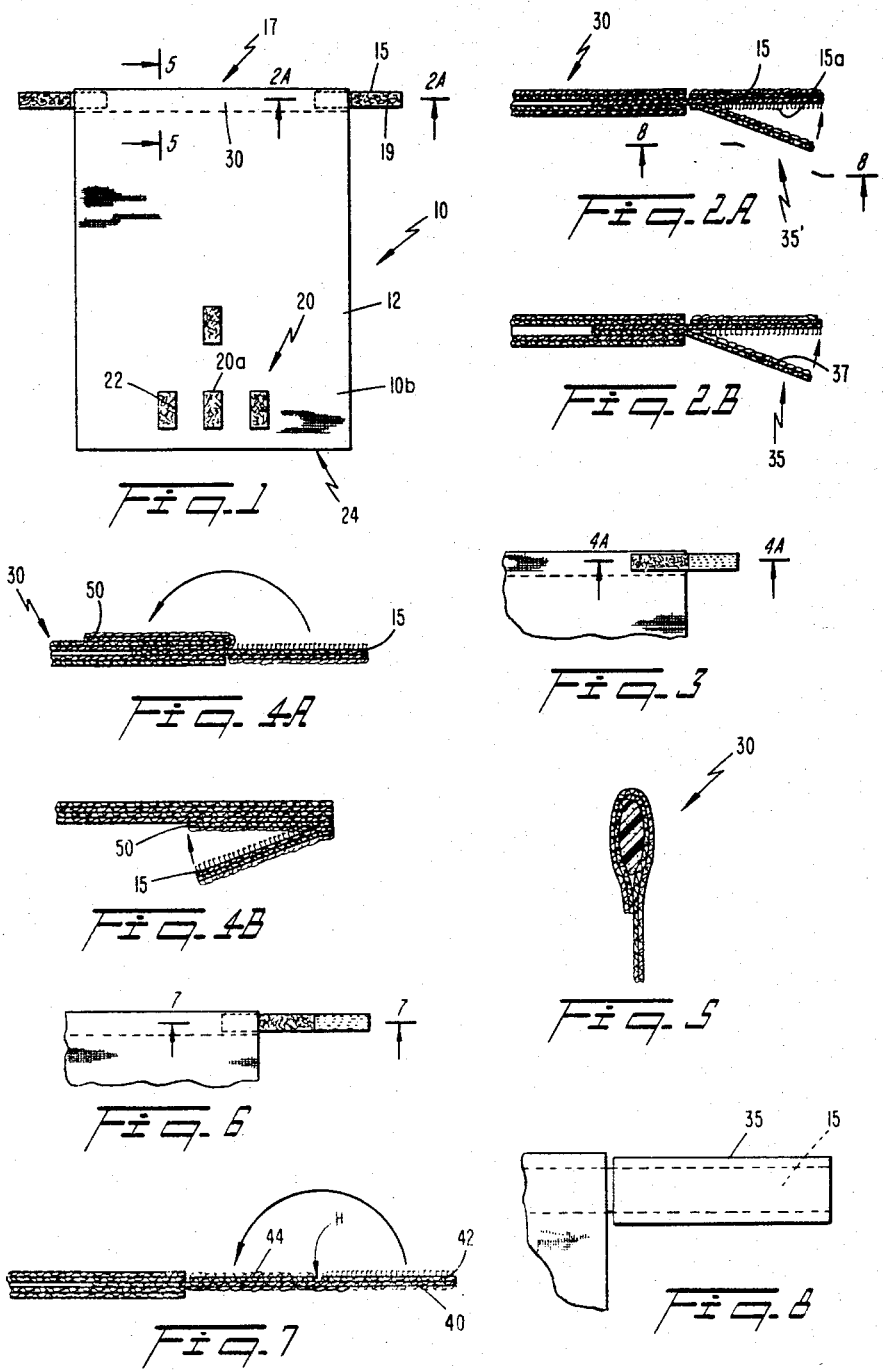

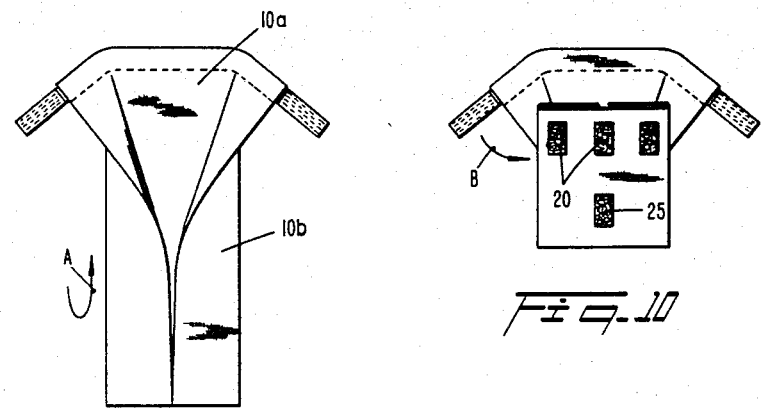
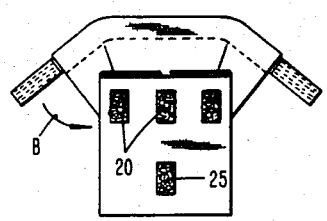
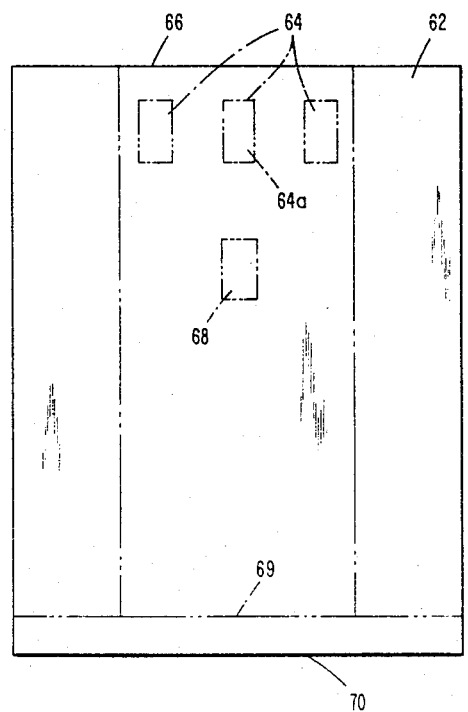
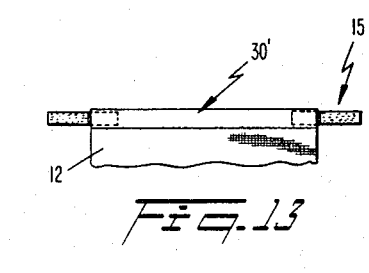

ADJUSTABLE DIAPER WITH A BACKBAND AND FASTENING PROTECTION MEANS

RELATED APPLICATIONS

This is a continuation-in-part application of my copending patent application, Ser. No. 315,049, filed on Oct. 26, 1981.

TECHNICAL FIELD

This invention generally relates to diapers and to fastening means therefor, and more particularly to washable diapers having a novel fastening arrangement that enables the diaper to accommodate infant growth with protective cover means for the fastening arrangement.

BACKGROUND ART

In my copending U.S. patent application identified above, there is disclosed a washable diaper having a novel fastening arrangement enabling the diaper to swaddle newborn infants with the ability to expand for diapering larger infants. Briefly, my prior diaper includes a first set of elongated female Velcro ® type fastening strips attached adjacent one transverse edge of the diaper. A set of second fastening strips or squares positioned in longitudinal alignment with the fastening strips and inwardly spaced therefrom on the diaper surface is provided to accommodate newborn infants. Male Velcro ®-type attachment tabs secured to the opposite transverse diaper edge are engageable with either the first or second set of fastening strips to diaper the infant in snug fitting relationship.

While my prior diaper is fully functional for the above mentioned purposes, I have noted that the attachment area of the tabs to the diaper edge tends to weaken after prolonged daily diaper use, requiring reattachment to function properly.

Another problem associated with my prior diaper relates to the amount of Velcro ® type tape employed thereon to perform diapering in the above adjustable manner. Since the Velcro ® type tape is a relatively expensive form of attachment means, it is desirable to improve upon the placement and the spacing of the strips in cooperation with the tabs to minimize the amount of material necessary to enable the diaper to function properly at reduced cost.

It is also desirable to prevent lint from collecting on the hook type projections of the male Velcro ® attachment tabs that would otherwise tend to deteriorate the adhesive effect of the diaper tabs and the diaper efficiency. Any type of tab protection means must be capable of prolonged and continuous use on the diaper for reliable and maintenance free operation.

It is accordingly an object of the present invention to provide an improved diaper which can be worn by newborn infants and thereafter expand to accommodate infant growth.

A further object is to provide a means for reinforcing the attachment tabs on the diaper for maintenance free and continued reliable use.

Still another object is to provide proper orientation of fastening strips and spacing therebetween on the diaper to minimize the amount of fastening material necessary for diaper performance.

Still a further object is to provide a means for preventing lint from collecting on the hook type projections of the attachment tabs.

Yet another object of the invention is to provide a diaper conversion kit to convert conventional diaper forms into the diaper of the invention.

DISCLOSURE OF THE INVENTION

A diaper, according to the present invention, comprises a substantially rectangular piece of absorbent washable fabric having opposite inner and outer surfaces. The inner surface is positionable to contact an infant's skin to be diapered. A pair of attachment tabs is secured to an upper portion of the diaper for engagement with a plurality of elongated fastening strips secured to the diaper outer surface adjacent a lower transverse edge thereof in spaced apart and substantially parallel relationship with each other. The tabs preferably carry resiliently deformable hook-like projections capable of meshing in fastening engagement with a plurality of loop-like projections provided on the fastening strips. The fastening strips extend vertically when positioned on the infant's abdomen and the tabs are variably positionable thereon to accommodate variations in infant size. A second strip inwardly spaced from the fastening strips enables the diaper to be folded to smaller size and is engageable with the tabs to accomodate newborn infants.

In one improvement feature of the invention, the tabs are of greater length than the lateral spacing between adjacent fastening strips to simultaneously engage adjacent fastening strips for secure attachment. The tabs are operatively attached to a backband along the upper edge portion of the diaper. The backband increases the upper edge thickness for reinforced tab attachement and improved absorbency.

Protective loop-bearing strips are operatively attached to the diaper adjacent the tabs and are positionable to mate with the tab hook-like projections to cover and prevent lint from accumulating on the hooks during diaper cleaning. In one embodiment of the invention, the protective strips are physically located outwardly from the diaper form to engage the tabs. In another embodiment, the protective strips are secured to the backband with reinforced through stitching.

According to the invention, the tabs and protective strips can be operatively attached to a separate backband strip that is attachable to the diaper upper edge for reinforcement.

A diaper conversion kit includes a pattern template having rectangular shapes printed thereon to define the size and location of the fastening strips and the attachment tabs when positioned flush on a conventional diaper form. A fold line printed on the template is provided to identify where the upper edge portion is folded onto itself to double thickness to form the backband. When positioned on the diaper form, the template enables proper marking of the diaper outer surface for subsequent tab and fastening strip attachment during home fabrication of the diaper.

Still other objects and advantages of the present invention will become readily apparent to those skilled in this art from the following detailed description, wherein I have shown only the preferred embodiments of the invention, simply by way of illustration of the best mode contemplated by me for carrying out my invention. As will be realized, the invention is capable of modifications in various aspects, all without departing from the invention. Accordingly, the drawings and description are to be regarded as illustrative in nature, and not as restrictive.

BRIEF DESCRIPTION OF THE DRAWING

FIG. 1 is a front view of the outer surface of the diaper in accordance with the present invention, showing the position of attachment tabs and fastening strips thereon;

FIG. 2A is a sectional view taken through the line 2A—2A of FIG. 1 showing reinforced attachment of the attachment tab to the diaper backband and one embodiment for mounting protective tab cover strips on the diaper;

FIG. 2B is similar to FIG. 2A showing another embodiment for mounting the protective strip to the diaper outside the backband;

FIG. 3 is a partial front view showing yet another embodiment for mounting the protective strip to the diaper;

FIG. 4A is a sectional view taken through the line 4A—4A of FIG. 3 showing a cross-sectional view of the embodiment shown in FIG. 3;

FIG. 4B is similar to FIG. 4A showing yet another embodiment of the invention;

FIG. 5 is a cross-sectional view taken through the line 5—5 of FIG. 1, showing one form of a reinforced backband provided in the invention;

FIG. 6 is another embodiment showing mounting of the protective strip for engagement with the attachment tab;

FIG. 7 is a cross-sectional view taken through the line 7—7 of FIG. 6;

FIG. 8 is a partial plan view of yet a further embodiment of the protective strip;

FIG. 9 is a partial perspective view of the diaper of the invention in partially folded position;

FIG. 10 is a partial perspective view of the diaper in a further folded position, after being folded to the position shown in FIG. 9;

FIG. 11 is yet another partial perspective view showing attachment of the attachment tabs in fastening engagement on the fastening strips;

FIG. 12 is a front view of a template pattern of the invention; and

FIG. 13 is a partial front view of another embodiment of the backband.

BEST MODE FOR CARRYING OUT THE INVENTION

Referring to FIG. 1, diaper 10 of the invention shown in an unfolded condition includes a substantially rectangular, conventional diaper form 12, such as a two-ply layer of washable cotton fabric of the sponge center type. Diaper 10 includes inner and outer surfaces 10a, 10b respectively, provided respectively on opposite sides of fabric 12 (see e.g. FIG. 9). Inner surface 10a is disposed adjacent the skin of an infant during wear, as explained below. In accordance with the invention, diaper 10 includes a unique fastening means allowing the diaper to be snugly fitted on infants of any size, in snug fitting relationship, in the manner set forth in detail in my co-pending U.S. patent application, Ser. No. 315,049, filed Oct. 26, 1981, the entire disclosure of which is specifically incorporated herein by reference.

To secure diaper 10 to the infant, a pair of attachment tab strips 15 is respectively secured to upper adjacent corners of fabric 12 along an upper edge portion 17 of the diaper (see FIG. 1). Tabs 15, as shown for example in FIG. 2a, respectively include on one elongated rectangular surface thereof a plurality of resiliently deformable hook-like projections 15a defining an attachment surface 19. Each tab 15 projects laterally outward from upper edge 17 in an unfastened position (FIG. 1) with the surface 19 facing in the direction of inner surface 10a. The tabs 15 are preferably male Velcro ® tape of the type available from Velcro ® U.S.A. Inc., New York, N.Y., or Aplix ® tape, sold by Aplix ® Inc., Pelham, N.Y.

To provide adjustable attachment of diaper 10 to accomodate infants of any size, three elongated fastening strips 20 are provided on outer surface 10b for mating engagement with tabs 15. Each strip 20 is a preferably rectangular and includes a plurality of loop-like projections 22 on the exposed surface thereof (FIG. 1), such as female Velcro ® tape or Aplix ® tape, which provide excellent meshing engagement and gripping characteristics with hook projections 15a. Strips 20 are preferably secured to outer surface 10b with through stitching and extend longitudinally along lower edge portion 24 of diaper 10, in a laterally spaced apart and parallel relationship to each other.

Prior to placing larger size infants on diaper 10, the longitudinally extending side panel portions of diaper 10 are folded onto inner surface 10a over the center panel portion, as shown in FIG. 9. The infant's bottom is then placed upon the center portion of diaper 10. The lower edge portion 24 is now folded upwardly between the infant's legs in the direction of arrow A (FIG. 9) to cover the infant's abdominal area and to thereby expose fastening strips 20 and 25 which advantageously do not contact the skin. Upper edge portion 17 extends around the infant's lower back area at waist level; thereafter, attachment tabs 15 are brought forward, in the direction of arrow B (FIG. 10), for secure attachment to the fastening strips 20 (FIG. 11). Diaper fastening in this manner provides a tighter bind around the legs to retain moisture, without causing discomfort to the infant, due to the selective positioning of tabs 15 on the strips 20.

More specifically, in the diapered position described above, fastening strips 20 are vertically oriented to allow adjustable positioning of tabs 15 on the strips to accommodate infants of any size. For example, attachment tabs 15 can be positioned on strips 20 adjacent lower edge 24 to diaper larger infants. For smaller infants, tabs 15 advantageously contact portions of strips 20 located inward from edge 24 to reduce diaper size for comfortable and proper wear. Of course, depending on infant size, different strips 20 can be engaged with tabs 15 in a rapid and easy fashion and at no time contact the infant's skin.

In accordance with the invention, the exposed length of tabs 15 (i.e. hook bearing attachment surfaces 19) is greater than the lateral spacing between adjacent strips 20. This relationship between the tab length and strip spacing advantageously allows the entire tab to securely engage the strips in secure and, in this manner, eliminates any free tab ends that might otherwise dangle on the diaper, leading to undesirable detachment between the tabs 15 and strips 20 by the infant.

The lateral spacing between adjacent strips 20 is preferably one and one quarter inches; each fastening strip is two inches in length and each tab length is two to three inches to obtain the best attachment conditions for infants of all sizes, while minimizing the amount of tape necessary to manufacture diaper 10.

To diaper newborn or small infants, lower edge portion 24 and strips 20 are first folded in the direction of inner surface 10a along the transverse fold region F (located between strips 20 and 25), as shown and described in the aforementioned copending application. Although such folding exposes fastening strips 20 to the infant's bottom, the side panel portions of diaper 10 are thereafter folded to cover the strips and to prevent contact with the infant's skin. It will be appreciated that a much smaller diaper 10 with increased absorbency (due to the increased folding thickness obtained with lower edge portion 24 positioned adjacent the stomach) is provided for the newborn infant in comparison with the diaper shown in FIG. 10 which accomodates larger infants, as discussed above. This feature is particularly important for diapering newborn infants, who spend considerable time lying on their stomachs. In addition, since strips 20 are laterally spaced from each other, they are capable of bunching together (i.e. accordion effect) to achieve the necessary fit.

The baby is then placed upon the smaller diaper and the lower diaper portion is raised upwardly to cover the infant's abdominal area, as discussed in connection with the larger diaper of the invention. In the folded position, the second fastening strip 25, discussed above, is now exposed outwardly from the infant. Attachment tabs 15 are then brought forward into fastening engagement with the strip 25 to complete diapering.

To diaper newborn infants, diaper 10 of the invention requires only one second fastening strip 25, in comparison with the arrangement of strips disclosed in my prior patent application mentioned above. In part, only one strip is necessary in view of the increased tab length of tabs 15 which can accomodate increased infant growth about the waist. This feature further minimizes the amount of tape necessary to manufacture diaper 10 and the amount of stitching required, to further reduce manufacturing cost. The length of second strip 25 is equal to the length of strips 20 (i.e. two inches) and is spaced inwardly from the center strip 20a by approximately two inches longitudinal alignment therewith.

The aforementioned size and spacing relationship of fastening strips 20 and 25 uniquely cooperate with tabs 15 to provide a rectangular attachment surface area on the infant's abdomen of approximately six inches by six inches (see FIG. 11) with a minimum amount of fastening tape. In view of the above sizes of tabs 15 and strips 20 and 25, it can be seen that a three-quarter inch wide roll of tape requires diaper 10 to include only approximately nine and three-quarter square inches of tape to provide reliable and adjustable fastening engagement over an attachment surface area four times as large.

Due to repeated and frequent use of diaper 10, a backband 30 is provided along upper edge portion 17 of the diaper to provide additional strength for attachment of tabs 15 and greater moisture retention within the diaper. In one preferred embodiment of diaper 10, backband 30 is formed by folding upper edge portion 17 onto itself to double thickness and securing the portions together with through stitching, resulting in a backband of approximately four ply thickness when a two-ply diaper form 12 is used (see e.g. FIG. 2a or 5). As shown in FIG. 2, backbank 30 enables tab 15 to be inserted into the band and secured with through stitchery. This unique cooperation between the tabs 15 and backband 30 enables the tabs to remain securely attached to diaper 10 throughout prolonged and continuous use. Additionally, the reinforcement of upper edge 17 obtained with backband 30 serves to maintain the diaper shape and to prevent fraying. This feature is of particular importance since the greatest amount of stress imposed on diaper 10 is in the backband area that is constantly pulled as the diaper is fitted to the infant.

FIG. 13 illustrates another embodiment of backband 30, designated with reference numeral 30'. Backband 30' includes a separate strip of fabric such as nylon or polyester having equal or greater strength than fabric 12. Backband 30', secured to upper edge portion 17 overlaps the upper edge and the juxtaposed end of tabs 15 and is secured thereto with through stitching to obtain the improved reinforcement and moisture retention conditions described above. In accordance with another feature of the invention, backband 30' carries attachment tabs 15, as shown in FIG. 13, and can be secured to upper edge portion 17 with a stitch that is entirely removable simply by applying tension to one end of the stitching thread (e.g. a chainstitch). This feature allows backband 30' and tabs 15 to be removed from upper edge portion 17 after a prolonged period of use for recycling on other diaper forms. In this manner, it will be recognized that tabs 15 detach with backband 30' when removal occurs, although the tabs are preferably also secured to the upper edge portion 17 with chainstitching for improved reinforcement during use on the diaper form.

As shown in FIGS. 2a and 4a, for example, the surface of tabs 15 opposite the hook bearing surface 19 can be provided with a strip of loop carrying tape (i.e. female Velcro ® or Aplix ® tape) 33. Strips 33 enable one of the tabs 15 to engage the other on strips 20 or 25 when desired. Additionally, diapers 10 can be easily stacked by fastening together tabs 15 of one diaper with strips 33 of another for storage simply doubled or for improved absorbency.

To prevent lint from collecting in the hook-like projections 15a of tabs 15 repetitive washing and the like, protective cover means is provided. In one embodiment of the invention, shown in FIG. 2B, the protective cover means includes a protective strip 35 of approximately the same as tab 15. Protective strip 35 is preferably female Velcro ® or Aplix tape carrying loop-like projections 37. As shown in FIG. 2B, each tab 15 overlaps with a strip 35 so that hook projections 15a and loop projections 37 face each other outside diaper form 12 in complete contacting registration. Corresponding ends of tabs 15 and strips 35 inserted within backband 30 or 30' are secured thereto with through stitching for improved reinforcement. Alternatively, as shown in FIG. 2B, a protective strip 35' of shorter length than strip 35 is attached at one end thereof to tab 15 with a single line of through stitching outside upper edge portion 17 so that loop-like projections 37 and hook-like projections 15a face each other in the manner described above.

Protective strips 30 contact with attachment surface 19 of tabs 15 protects hook projections 15a during diaper washing and the like. Set up is made simply by gently pressing the protective strip 35 and the associated tab together prior to cleaning. Moreover, since the hooks 15a and loops 37 face each other on the overlapping strips biased together with the through stitching, a self-closing action is obtained with the above described embodiment. Further, by physically locating the protective strips 35 outside diaper form 12, the soiled diaper can be handled (e.g. toilet rinsing) without physically contacting the diaper form simply by engaging the tabs and protective strips. It will be further appreciated that strip 35 and tab 15 can be attached together to secure diaper 10 to a clothesline.

In another embodiment of the protective cover means, as shown in FIG. 7, a first strip 40 of loop carrying tape is secured to backband 30 or 30' with stitching and projects laterally outwardly therefrom. A second strip 42 shorter than the first strip 40 is stitched or otherwise secured to the first strip on the surface opposite the loop bearing surface. Second strip 42 is preferably Velcro ® or Aplix tape carrying hook projections to form the attachment tab 15. A third strip 44 shorter than the first strip 40 and carrying loop-like projections is attached to the first strip adjacent the second strip 42, forming a hinge H. It will be appreciated that second and third strips 42, 44 are foldable to mate with each other (i.e. between the hook and loop portions) about hinge point H to selectively cover and uncover tab 15. In this embodiment of the invention, the protective cover means is also located outside diaper form 12 for improved soiled diaper handling. This unique closure arrangement with hinge H is not self-closing, thus avoiding the need for physically detaching the third strip 44 from second strip 42 after washing (i.e. attachment tab 15) after initial detachment prior to diapering the infant.

In a further embodiment of the protective cover means, attachment tab 15 is secured to backband 30 or 30' as described in connection with the embodiment shown in FIG. 2A. As shown in FIG. 4A, a protective loop-bearing strip 50 is completely stitched down on backband 30 or 30' with through stitching adjacent the upper corners of diaper form 12. In this embodiment of the invention, hook projections 15a on tabs 15 are protected by positively folding the tab onto the loops of protective strips 50. This embodiment is particularly preferred for use when a separate backband 30' is to be provided in diaper 10 of the invention, as described above. It will be further appreciated that protective strip 50 is fully attached to backband 30' on all sides with through stitching, together with a part of attachment tab 15. Greater reinforcement of the strip 50 occurs when backband 30' and the protective strip are attached to the upper edge portion 17; the resulting attachment is preferred since the protective strip on the backband undergoes greater stress during the detaching action of tab 15 therefrom.

In an alternative embodiment to the invention shown in FIG. 4A, attachment tab 15 can be secured to protective strip 50 and to backband 30 or 30' by mounting the tab directly onto the strip along the outer corner side with a single line of through stitching, as shown in FIG. 4B. In this embodiment, the hook projections 15a are biased into covering position with the loop projections on strip 50 to achieve a self-closing action, if preferred.

FIG. 5 shows another modification of backband 30, requiring a length of sponge type material to be positioned along upper edge 17 prior to folding the edge to double thickness. It will be recognized that inclusion of the sponge layer in the above manner improves the moisture absorbency of the backband to prevent moisture from escaping the diaper and spreading up the infant's back.

FIG. 8 is an illustration of another aspect of the invention showing the use of the protective loop bearing cover strips discussed above being wider than the corresponding attachment tab 15. This feature ensures complete closure and protection of hook projections 15a from the external environment through full contacting registration.

From the foregoing, it can be seen that diaper 10 of the invention is capable of easy and reliable use on infants of any size, due to the features of and spacing between strips 20 and 25 in cooperation with tabs 15, as described above. Backband 30 or 30' provided along upper edge portion 17 reinforces tabs 15 and the protective strips, as described above, which is essential for prolonged daily use considering the constant opening and closing action both the tabs and the protective strips are required to undergo. In addition, the features of the invention set forth above are easily attachable to conventional diaper forms, resulting in cost effective modification of existing diapers and manufacture of new diapers with the above improvement features.

To permit fabrication of diaper 10 of the invention in the home, a pattern template 60 is provided, as shown in FIG. 12. Templet 60 basically includes a rectangular sheet of material 62, such as paper, of approximately the same size as the diaper form 12. A first set of three rectangular shapes 64 is provided adjacent edge 66 of sheet 62 in laterally spaced apart and parallel relationship to each other. A rectangular shape 68 equal in size to shapes 64 is printed on sheet 62 in spaced apart and longitudinal alignment with the center shape 64a. A fold line 69 extends parallel to the opposite transverse edge 70 of sheet 62. It will be appreciated that when template 60 is positioned on a diaper form 12 in contacting registration, shapes 64, 68 and line 69 can be easily transferred onto outer surface 10b of diaper form 12 to enable identification of location of fastening strips 20 and 25 and backband 30 for subsequent attachment to the diaper form. Suitable parallel lines can also be provided on template 60 adjacent line 69 to denote location of a separate backband 30'. The diaper conversion kit incorporating pattern template 60 can variably include the precut tabs and strips, the diaper form or preformed backband 30' including the mounted tabs for home preparation.

In this disclosure, there are shown and described only the preferred embodiments of the invention, but, as aforementioned, it is to be understood that the invention is capable of changes or modifications within the scope of the inventive concept as expressed herein. For example, each strip 64 and strip 68 on template 60 can include concentrically drawn additional strips of different size to accommodate and provide different size strips on the diaper.

I claim:

1. A diaper, comprising:
   (a) a substantially rectangular piece of absorbent washable fabric having opposite inner and outer surfaces, said inner surface positionable to contact a wearer's skin to be diapered;
   (b) a pair of attachment tabs attached to an upper edge portion of the fabric, each tab carrying a plurality of resiliently deformable, hook-like projections projecting outward from a surface of the tab;
   (c) fastening means secured to the outer surface of the fabric, adjacent a lower transverse edge thereof for engaging the attachment tabs to secure the diaper of the wearer, said fastening means having a surface carrying a plurality of resiliently deformable, loop-like projections for engagement with the tab surfaces; and (d) self-closing protective cover means carrying loop-like projections one edge of each tab and one end of its cover means being joined such that the surface areas of the tab and cover means are maintained face to face, in juxtaposition and coextensive and thereby tend to self-close, insulating the hook-like projections of the tabs from lint, during diaper cleaning.

2. A diaper according to claim 1, wherein said upper edge portion is back-folded to establish a double ply portion, said double ply portion being secured with through stitching to define a back band positionable around the wearer's back at waist level during wear for improved absorbency and for reinforcement of said upper edge.

3. A diaper according to claim 1 or 2, wherein each attachment tab is secured at an upper corner of the diaper to project laterally and outwardly therefrom, said protective means including a strip of material carrying the loop-like projections and being approximately the same size as the tab, said protective strip adapted to engaging with hook-like projections of the tab.

4. A diaper according to claim 1 or 2, wherein said protective cover means includes a strip of material carrying the loop-like projections, said protective strip being attached at one end thereof to the attachment tab outside the upper edge portion of and extending outwardly from the diaper with the loop-like projections of the cover means and the hook-like projections of the tab facing each other.

5. A diaper according to claim 1 or 2, wherein said protective cover means has a width greater than a width of said tabs.

6. A diaper according to claim 2; wherein each said tab extends outwardly from within the double ply portion of said diaper, said cover means being sewn to a portion of said tab outside said diaper.

7. The diaper of claim 4, wherein said cover means is stitched directly to said tab.

8. The diaper of claim 4, wherein said cover means and said tab means are stitched together and are in contact with each other at an adjacent edge of said diaper.

9. A diaper comprising:
(a) a substantially rectangular piece of absorbent washable fabric having opposite inner and outer surfaces, said inner surface positionable to contact a wearer's skin to be diapered;
(b) a pair of attachment tabs attached to an upper edge portion of the fabric, each tab carrying a plurality of resiliently deformable, hook-like projections projecting outward from a surface of the tab;
(c) fastening means secured to the outer surface of the fabric, adjacent a lower transverse edge thereof for engaging the attachment tabs to secure the diaper to the wearer, said fastening means having a surface carrying a plurality of resiliently deformable, loop-like projections for engagement with the tab surfaces; and
(d) protective cover means carrying loop-like projections, insulating the hook-like projections of the tabs from lint, during diaper cleaning;
wherein said protective cover means includes a first strip of material having one end attached to the upper edge portion of the diaper to project laterally outwardly therefrom, a second strip of material shorter than the first strip and carrying loop-like projections, and a third strip shorter than the first strip and carrying hook-like projections, said second and third strips being attached to the first strip to define a hinge, whereby said second and third strips selectively pivot about the hinge to enable the second and third strips to engage.

10. A diaper comprising:
(a) a substantially rectangular piece of absorbent washable fabric having opposite inner and outer surfaces, said inner surface positionable to contact a wearer's skin to be diapered;
(b) backband means back-folded along an upper edge portion of the diaper to increase the thickness of the upper edge and to improve the absorbency and the strength thereof, said backband means being positionable to contact the wearer's back at waist level;
(c) a pair of attachment tabs secured to the backband means, each said tab carrying a plurality of resiliently deformable hook-like projections projecting upwardly from a tab surface;
(d) fastening means secured to the outer surface of the diaper adjacent the lower transverse edge thereof for engaging the attachment tabs to secure the diaper to the wearer, said fastening means carrying a plurality of resiliently deformable loop-like projections for engagement with the attachment tabs;
(e) protective cover means attached to the backband means adjacent the attachment tabs, said attachment tabs being slightly narrower than the backband means and said protective cover means, said protective cover means carrying loop-like projections engageable with the hook-like projections on the tabs to prevent excessive lint accumulation on the hook-like projections from occurring during diaper cleaning.

11. A diaper according to claim 10, wherein said backband means includes a strip of fabric separate from the upper edge portion of the diaper and of approximately the same length as the upper transverse edge of the diaper, said backband strip carrying the attachment tabs and the protective means.

12. A diaper according to claim 11, wherein said backband strip is secured to the upper edge portion of the diaper with a removable stitch being operable to detach the backband from the diaper by pulling one thread in the stitch to thereby remove the entire stitch.

13. A diaper according to claim 12, wherein said backband strip is secured to the diaper with a chain stitch.

14. A diaper comprising:
(a) a substantially rectangular piece of absorbent washable fabric having opposite inner and outer surfaces, said inner surface positionable to contact a wearer's skin to be diapered;
(b) backband means back-folded along an upper edge portion of the diaper to increase the thickness of the upper edge and to improve the absorbency and the strength thereof, said backband means being positionable to contact the wearer's back at waist level;
(c) a pair of attachment tabs secured to the backband means, each said tab carrying a plurality of resiliently deformable hook-like projections;
(d) fastening means secured to the outer surface of the diaper adjacent the lower transverse edge thereof for engaging the attachment tabs to secure the diaper to the wearer, said fastening means carrying a plurality of resiliently deformable loop-like projections for engagement with the attachment tabs;

(e) self-closing protective cover means attached to the backband means adjacent the attachment tab, said protective cover means carrying loop-like projections engageable with the hook-like projections on the tabs to prevent excessive lint accumulation on the hook-like projections from occuring during diaper cleaning;

(f) wherein each tab includes one end secured to the protective cover means with through stitching to bias the hook-like projections on the tabs in the direction of the loop-like projections on the protective cover means to cause the tabs and cover means to tend to self-close.

15. A diaper, comprising:
(a) a substantially rectangular piece of absorbent washable fabric having opposite inner and outer surfaces, said inner surface positionable to contact a wearer's skin to be diapered;
(b) a pair of attachment tabs attached to an upper edge portion of the diaper, each tab carrying a plurality of resiliently deformable, hook-like projections;
(c) fastening means secured to the outer surface of the diaper adjacent a lower transverse edge thereof for engaging the attachment tabs to secure the diaper to the wearer, said fastening means having a surface carrying a plurality of resiliently deformable, loop-like projections for engagement with the tab surfaces; and
(d) protective cover means carrying loop-like projections to couple with the hook-like projections of the tab, the cover means being located substantially entirely on a surface of said fabric, one end of said cover means being attached to only one end of said tab, the remaining end of said tab being free floating.

16. A diaper according to claim 15, wherein each said said tab extends outwardly from the upper edge portion of said fabric and is adapted to be back folded into engagement with said cover means.

17. A diaper according to claim 15, wherein each said tab extends inwardly from the upper edge portion of said fabric to be engaged with said cover means.

18. A diaper comprising:
(a) a substantially rectangular piece of absorbent washable fabric having opposite inner and outer surfaces, said inner surface positionable to contact a wearer's skin to be diapered;
(b) a pair of attachment tabs attached to an upper edge portion of the diaper, each tab carrying a plurality of resiliently deformable, hook-like projections projecting outward from a surface of the tab;
(c) fastening means secured to the outer surface of the diaper adjacent a lower transverse edge thereof for engaging the attachment tabs to secure the diaper to the wearer, said fastening means having a surface carrying a plurality of resiliently deformable, loop-like projections for engagement with the tab surfaces;
(d) protective cover means attached to the tabs adjacent edges of the diaper and carrying loop-like projections to couple with the hook-like projections of the tabs thereby insulating the hook-like projections of the tabs from lint, during diaper cleaning;
(e) wherein said upper edge portion is reinforced to establish a double ply portion, said double ply portion being secured to the diaper;
(f) wherein each said tab and said cover means extends outward from within the double ply portion of said diaper.

19. A diaper comprising:
(a) a substantially rectangular piece of absorbent washable material having opposite inner and outer surfaces, said inner surface positionable to contact a wearer's skin to be diapered;
(b) a pair of attachment tabs secured to an upper edge portion of one side of the diaper, each tab carrying a plurality of resiliently deformable hook-like projections;
(c) fastening means secured to the outer surface of the diaper adjacent a lower transverse edge thereof for engaging the attachment tabs to secure the diaper to the wearer, said fastening means carrying deformable loop-like projections to couple to the hook-like projection of said tab means; and
(d) self-closing cover means having one end thereof secured at said one side of the diaper adjacent one end of said tab means and carrying deformable loop-like projections adapted to couple to the hook-like projections of said tab means, the remaining ends of said cover means and of said tab means being free floating, said cover means and tab means positioned to be maintained face to face, in juxtaposition and coextensive, and thereby tend to self-close.

20. A garment, comprising:
a piece of fabric;
an attachment tab carrying hook-type filamentary material;
a cover means carrying loop-type filamentary material;
the attachment tab and the cover means having only one of their ends joined together and to the fabric with the remaining ends of at least one of said tab and cover means being free floating such that the hook-type and loop-type filamentary materials are maintained face to face, in juxtaposition and coextensive, whereby the attachment tab and cover means tend to self-close and couple to each other.

21. The garment of claim 20, wherein said cover means is positioned substantially entirely on said fabric.

22. The garment of claim 20, wherein said tab and said cover means extend outward from one side of said fabric.

23. The garment of claim 22, wherein said cover means is under said tab.

* * * * *

UNITED STATES PATENT AND TRADEMARK OFFICE
CERTIFICATE OF CORRECTION

PATENT NO. : 4,537,591
DATED : 8/27/85
INVENTOR(S) : Fredrica V. COATES,

It is certified that error appears in the above-identified patent and that said Letters Patent is hereby corrected as shown below:

On the title Item [56] should appear as shown below:

References Cited
U.S. PATENT DOCUMENTS

| | | | |
|---|---|---|---|
| 3,063,749 | 11/1962 | Struble et al | 297/220 |
| 3,081,772 | 4/1960 | Brooks et al | |
| 3,089,494 | 1/1962 | Schwartz | |
| 3,141,461 | 7/1964 | Farris | |
| 3,150,664 | 9/1964 | Noel | |
| 3,359,980 | 12/1967 | Rosenblatt | |
| 3,554,195 | 1/1971 | Murdoch | |
| 3,616,498 | 11/1971 | Rosenthal | |
| 3,618,608 | 11/1971 | Brink | |
| 3,653,381 | 4/1972 | Warnken | |
| 3,955,575 | 5/1976 | Okuda | |
| 4,051,544 | 10/1977 | Kallman | |
| 4,051,854 | 1/1976 | Aaron | |
| 4,055,873 | 11/1977 | Kallman | |
| 4,058,853 | 11/1977 | Boxer et al | 428/ 100 |

Signed and Sealed this

Thirty-first Day of December 1985

[SEAL]

Attest:

DONALD J. QUIGG

Attesting Officer   Commissioner of Patents and Trademarks